United States Patent [19]

Scholz et al.

[11] Patent Number: 5,759,691

[45] Date of Patent: Jun. 2, 1998

[54] PHOSPHORUS-MODIFIED COATING COMPOSITIONS, A PROCESS FOR THEIR PREPARATION, AND THEIR USE

[75] Inventors: Guido Scholz, Burgkirchen; Sebastian Hörold, Erftstadt; Wolf-Dieter Pirig, Euskirchen, all of Germany

[73] Assignee: Hoechst Aktiengesellschaft, Frankfurt, Germany

[21] Appl. No.: 810,550

[22] Filed: Mar. 3, 1997

[30] Foreign Application Priority Data

Mar. 6, 1996 [DE] Germany .................. 196 08 611.6

[51] Int. Cl.$^6$ .................. C09D 5/18; C09D 163/00; C08G 59/40; C08K 5/5333
[52] U.S. Cl. .................. 428/413; 428/415; 428/417; 428/901; 528/91; 528/103; 528/108; 528/398; 528/399; 521/178; 521/179; 521/180; 525/507; 525/523
[58] Field of Search .................. 428/413, 415, 428/417, 901; 528/103, 91, 108, 398, 399; 521/178, 179, 180; 525/507, 523

[56] References Cited

U.S. PATENT DOCUMENTS

| | | | |
|---|---|---|---|
| 3,334,110 | 8/1967 | Schramm | 260/307 |
| 3,607,795 | 9/1971 | Nolken | 260/2.5 |
| 3,629,163 | 12/1971 | Nolken | 260/2.5 |
| 4,289,812 | 9/1981 | Martin | 427/379 |
| 4,529,467 | 7/1985 | Ward et al. | 156/307.3 |
| 4,952,646 | 8/1990 | Weil et al. | 525/507 |
| 5,364,893 | 11/1994 | von Gentzkow et al. | 523/429 |
| 5,587,253 | 12/1996 | Von Gentzkow et al. | 428/413 |

FOREIGN PATENT DOCUMENTS

| | | |
|---|---|---|
| 0142074 | 5/1985 | European Pat. Off. . |
| 0384939 | 9/1990 | European Pat. Off. . |
| 0409308 | 6/1995 | European Pat. Off. . |
| 735119 | 3/1996 | European Pat. Off. . |
| 2757733 | 7/1978 | Germany . |
| 94/21703 | 9/1994 | WIPO . |

OTHER PUBLICATIONS

*Lackkunstharze* (Wagner/Sarx), 5th ed., Carl Hanser Verlag (1971), pp. 174–194.

Bald, G., et al., *Angewandte Makromol. Chem.* 44:151–163 (1975).

*Primary Examiner*—Frederick Krass
*Attorney, Agent, or Firm*—Connolly and Hutz

[57] ABSTRACT

The invention relates to an expandable, halogen-free, flame-retardant coating composition comprising epoxy resins, polyphosphoric/polyphosphonic esters and a curing agent, which composition comprises from 75 to 95 parts by weight of epoxy resin and from 5 to 25 parts by weight of polyphosphoric/polyphosphonic ester and wherein the overall weight ratio of epoxy resin and polyphosphoric/polyphosphonic ester to curing agent is (1.1 to 10) to 1. The invention likewise relates to a process for preparing such coating compositions and to their use.

14 Claims, No Drawings

PHOSPHORUS-MODIFIED COATING COMPOSITIONS, A PROCESS FOR THEIR PREPARATION, AND THEIR USE

The invention relates to expandable, halogen-free, flame-retardant coating compositions comprising epoxy resins and polyphosphoric/polyphosphonic esters and a curing agent, to a process for preparing such coating compositions and to their use.

Coating compositions based on epoxy resins, and epoxy resin molding compositions, have been known for a long time. The epoxy resins employed as starting materials are nowadays widely employed for preparing epoxy resin molding compositions and for coating to a high level of thermal, mechanical and electrical properties, and for producing laminates.

The various starting components (also called epoxy resin component) can be reacted, to form the corresponding coating compositions, either by using curing agents (also called curing component), for example carboxylic anhydrides, amines, phenols or isocyanates, or by ionic polymerization.

The epoxy resins are generally easy to process, since in the initial state they are of low molecular weight or are oligomeric, and have a low viscosity at normal processing temperature. They lend themselves readily to casting or can be employed in saturation and impregnation processes.

In accordance with the required areas of application (for example flooring coatings on oil drilling platforms, carparks, airports, etc.) it is necessary for such coating compositions to be made flame-resistant. Epoxy resins and epoxy resin molding compositions for such applications, i.e. as a coating composition, must therefore be self-extinguishing and must not transmit fire.

Epoxy resins and epoxy resin molding compositions are nowadays made flame-resistant using halogen-containing, especially bromine-containing, aromatic components. Such components frequently include antimony trioxide as synergists, and are incorporated into the epoxy resin. The carbonization or combustion of these epoxy resins treated in this way, however, gives rise to decomposition products which are highly objectionable from an ecological or toxicological standpoint.

For instance, EP-A-0 142 074 describes an intumescent composition comprising, inter alia, an epoxy resin and also compounds of phosphorus, zinc or boron, which when subjected to decomposition at great heat gives off a series of organic and inorganic, ecologically and toxicologically objectionable products.

There is therefore a considerable need for coating compositions that are based on epoxy resins and possess a high level of flame resistance, but which neither comprise nor, on decomposition under the effect of heat, give off halogen-containing components or other ecologically or toxicologically objectionable products.

The object of the invention, therefore, was to provide expandable, flame-retardant coating compositions which exhibit high flame resistance and which do not give off ecologically or toxicologically objectionable products on decomposition under the effect of heat. Furthermore, it should be possible to prepare the coating compositions simply and inexpensively, and to use them in a simple manner.

The present invention therefore provides an expandable, halogen-free, flame-retardant coating composition of the type described at the outset, which composition comprises from 75 to 95 parts by weight of epoxy resin and from 5 to 25 parts by weight of polyphosphoric/polyphosphonic ester, and wherein the overall weight ratio of epoxy resin and polyphosphoric/polyphosphonic ester to curing agent is (1.1 to 10) to 1.

The expandable, halogen-free, flame-retardant coating composition preferably comprises up to 65 parts by weight of further ingredients and fillers.

The expandable, halogen-free, flame-retardant coating composition preferably comprises from 0.05 to 10% by weight of phosphorus.

The expandable, halogen-free, flame-retardant coating composition particularly preferably comprises from 2 to 7% by weight of phosphorus.

The halogen-free epoxide compounds employed in accordance with the invention (also referred below as polyepoxide compounds) may be saturated or unsaturated and may be aliphatic, cycloaliphatic, aromatic and/or heterocyclic. They may, furthermore, include substituents which do not give rise, under the conditions of mixing or of reaction, to disruptive side reactions, examples being alkyl or aryl substituents, ether groups or the like. It is also possible to use mixtures of different polyepoxide compounds. The mean molecular weight $M_n$ of these polyepoxide compounds can be up to about 9000, but is generally from about 150 to 4000.

These polyepoxide compounds are preferably polyglycidyl ethers based on polyhydric, preferably dihydric, alcohols, phenols, hydrogenation products of these phenols and/or on novolaks (reaction products of mono- or polyhydric phenols, such as phenol and/or cresols, with aldehydes, especially formaldehyde, in the presence of acidic catalysts), which are obtained in a known manner, for example by reacting the respective polyols with epichlorohydrin.

Particularly suitable polyhydric phenols are: resorcinol, hydroquinone, 2,2-bis (4-hydroxyphenyl)propane (bisphenol A), isomer mixtures of dihydroxydiphenylmethane (bisphenol F), 4,4'-dihydroxydiphenylcyclohexane, 4,4'-dihydroxy-3,3'-dimethyldiphenylpropane, 4,4'-dihydroxybiphenyl, 4,4'-dihydroxybenzophenone, 1,1-bis-(4-hydroxyphenyl)ethane, 1,1-bis(4-hydroxyphenyl)isobutane, 2,2-bis(4-hydroxy-tert-butylphenyl)propane, bis(2-hydroxynaphthylmethane, 1,5-dihydroxynaphthalene, tris(4-hydroxyphenyl) methane, bis(4-hydroxyphenyl) ether.

Among these, bisphenol A and bisphenol F are preferred.

Other suitable polyepoxide compounds are the polyglycidyl ethers of polyhydric aliphatic alcohols, such as 1,4-butanediol, 1,6-hexanediol, polyalkylene glycols, glycerol, trimethylolpropane, 2,2-bis(4-hydroxycyclohexyl)propane and pentaerythritol.

Further suitable polyepoxide compounds are (poly) glycidyl esters, which are obtained by reacting epichlorohydrin or similar epoxy compounds with an aliphatic, cycloaliphatic or aromatic polycarboxylic acid, such as oxalic acid, adipic acid, glutaric acid, phthalic, isophthalic, terephthalic, tetrahydrophthalic or hexahydrophthalic acid, 2,6-naphthalenedicarboxylic acid and dimerized fatty acids. Examples hereof are diglycidyl terephthalate and diglycidyl hexahydrophthalate.

Polyepoxide compounds which comprise the epoxide groups in random distribution along the molecule chain and which can be prepared by emulsion copolymerization using olefinically unsaturated compounds containing these epoxide groups, for example glycidyl esters of acrylic or methacrylic acid, can also be employed with advantage in some cases.

Examples of further polyepoxide compounds which can be used are those based on heterocyclic ring systems, such as, for example, hydantoin-epoxy resins, triglycidyl isocyanurate and/or oligomers thereof, triglycidyl-p-aminophenol, triglycidyl-p-aminodiphenyl ether, tetraglycidyldiaminodiphenylmethane, tetraglycidyldiaminodiphenyl ether, tetrakis(4-glycidyloxyphenyl)ethane, urazole epoxides, uracil epoxides and oxazolidinone-modified epoxy resins, and also polyepoxides based on aromatic amines, such as aniline, examples being N,N-diglycidylaniline, diaminodiphenylmethane and N,N'-dimethylaminodiphenylmethane or N,N'-dimethylaminodiphenyl sulfone.

Further suitable polyepoxide compounds are described in the "Handbook of Epoxy Resins" by Henry Lee and Kris Neville, McGraw-Hill Book Company, 1967, in the monograph by Henry Lee entitled "Epoxy Resins", American Chemical Society, 1970, in Wagner/Sarx "Lackkunstharze" [Synthetic Resins for Coatings], Carl Hanser Verlag (1971), 5th Edition, 174 ff., in Angew. Makromol. Chemie 44 (1975), pages 151 to 163, in DE-A-27 57 733 and in EP 0 384 939 A1, which is incorporated herein by reference.

Polyepoxide compounds which are preferably employed are bisglycidyl ethers based on bisphenol A, bisphenol F and bisphenol S (reaction products of these bisphenols and epichloro(halo)hydrin) or oligomers thereof, polyglycidyl ethers or phenol/formaldehyde novolaks and/or cresol/formaldehyde novolaks, and diglycidyl esters of phthalic, isophthalic, terephthalic, tetrahydrophthalic and/or hexahydrophthalic acid and of trimellitic acid, N-glycidyl compounds of aromatic amines and heterocyclic nitrogen bases, such as N,N-diglycidylaniline, N,N,O-triglycidyl-p-aminophenol, triglycidylisocyanurate and N,N,N',N'-tetraglycidylbis(p-aminophenyl)methane, hydantoin-epoxy resins and aracid-epoxy resins, and also di- and polyglycidyl compounds of polyhydric aliphatic alcohols such as 1,4-butanediol, trimethylolpropane and polyalkylene glycols.

In addition, oxazolidinone-modified epoxy resins are also suitable. Such compounds are already known (Angew. Makromol. Chem. 44 (1975), pages 151 to 163, and U.S. Pat. No. 3,334,110); an example thereof which may be mentioned is the reaction product of bisphenol A diglycidyl ether with diphenylmethane diisocyanate (in the presence of an appropriate accelerator).

In connection with the preparation of the novel coating composition, the polyepoxy resins as used for the present invention may be present individually or in a mixture.

The polyphosphoric/phosphonic ester is prepared, for example, in accordance with EP 0 409 308 B1, by reacting a phosphonic triester with phosphorus pentoxide (P$_2$O$_5$), and is of the formula

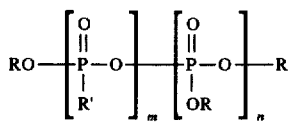

where R and R'=alkyl (preferably methyl, ethyl, propyl, butyl) or haloalkyl (such as 2-chloroethyl, 2-chloroisopropyl, 2,3-dichloroisopropyl) and (m+n)≧4 (mean chain length).

The arrangement of the phosphonic anhydride groups [RP(O)O] and phosphoric anhydride groups [ROP(O)O] within the oligomer and polymer chains is preferably random. Typically, the molar ratio of phosphonic to phosphoric acid groups, depending on the mean chain length, is from 1:1 to 1:2.

These polyphosphoric/phosphonic esters are notable for a high phosphorus content and hence very effective flame protection. Furthermore, they can be considered formally as mixed polyanhydrides of phosphonic and phosphoric esters, which react with epoxide groups to form phosphonic diesters and phosphoric triesters and which therefore, as described in EP 0 409 308 B1, are suitable as anhydride curing agents for epoxy resins.

A disadvantage of the alkylpolyphosphoric esters and alkylpolyphosphonic/phosphoric esters described therein is their high reactivity toward epoxy resins, which, after the curing agent and resin components have been mixed, remain for only a few seconds in a liquid and therefore processible state. In many cases, virtually immediate solidification takes place. This is especially disadvantageous for the preparation of coating compositions, since the resulting pot life is therefore too short.

In addition, the alkylpolyphosphoric esters and alkylpolyphosphonic/phosphoric esters are not easy for the user to handle, since they are highly sensitive to hydrolysis.

In accordance with the invention these disadvantages are overcome, in a process for preparing expandable, halogen-free, flame-retardant coating compositions comprising epoxy resins and polyphosphoric/polyphosphonic esters and a curing agent, by reacting, in a first reaction step, an epoxy resin with the polyphosphoric/polyphosphonic ester, and then, in a second reaction step, converting the reaction product into the coating composition with a curing agent.

This reaction of the epoxy resin with a substoichiometric amount of polyphosphonic/polyphosphoric ester produces a meltable and/or soluble, phosphoric-modified epoxy resin which is stable on storage (in solution if desired) and is easy to handle. In a second step, it can then be converted to the novel coating composition with a curing agent.

The first reaction step is preferably carried out in a solvent.

Aprotic polar solvents which can be employed are N-methylpyrrolidone, dimethylformamide, tetrahydrofuran, dioxane, dialkyl ethers, glycol ethers, ketones and/or esters.

Other solvents which can be employed are halogenated hydrocarbons and aliphatic, cycloaliphatic and/or aromatic hydrocarbons, individually or as mixtures.

The reaction in the first reaction step is preferably carried out at temperatures from −10° to +200° C.

The reaction is preferably carried out at temperatures from 20° to 100° C.

With particular preference, the reaction is carried out at temperatures from 50° to 80° C.

The reaction in the second reaction step is carried out at temperatures from 0° to 200° C.

This reaction is preferably carried out at temperatures from 30° to 150° C.

With particular preference, this reaction is carried out at temperatures from 70° to 120° C.

The term "curing" as used herein denotes the conversion of the soluble, meltable polyepoxides to solid, insoluble and infusible, three-dimensionally crosslinked products, generally with simultaneous shaping, in order to give, for instance, coatings, impregnated structures and adhesive bonds.

Examples of curing agents which can be employed are aliphatic, cycloaliphatic, aromatic and heterocyclic amines, such as bis(4-aminophenyl)methane, anilineformaldehyde resins, bis(4-aminophenyl) sulfone, ethylenediamine, 1,3-propanediamine, hexamethylenediamine, diethylenetriamine, triethylenetetramine, 2,2,4-trimethyl-1,6-diamine, m-xylylenediamine, bis(4-aminocyclohexyl)methane, 2,2-bis(4-aminocyclohexyl)propane, 3-aminomethyl-3,5,5-trimethylcyclohexylamine (isophoronediamine), polyamidoamines, polyphenols, such as hydroquinone, resorcinol, 2,2-bis(4-hydroxyphenyl)

propane (bisphenol A) and phenol-aldehyde resins, polycarboxylic acids and their anhydrides, for example phthalic anhydride, tetrahydrophthalic anhydride, hexahydrophthalic anhydride and pyromellitic anhydride. In addition to these it is also possible to use catalytic curing agents, such as cyanoguanidines, or Friedel-Crafts catalysts, such as boron trifluoride.

Where amines are used as curing agents, they are normally employed in an amount of from 0.75 to 1.25 equivalents per epoxide equivalent. In the case of polycarboxylic acids or their anhydrides, from 0.4 to 1.1 equivalents are used per epoxide equivalent.

As a further, additive curing component (i.e. in addition to the actual curing agent) it is possible to employ heterocyclic polyamines which have urea groups. Other aromatic polyamines, such as 4,4'-diaminodiphenylmethane, 4,4'-diaminodiphenyl sulfone, and/or other heterocyclic polyamines, can also be employed in the curing agent mixture in a proportion by weight of up to a maximum of 30%.

The novel coating composition preferably comprises, as further additives, accelerators, fillers, pigments, flexibilizers and/or reactive diluents.

Suitable accelerators are principally imidazole derivatives, for example 2-methylimidazole, 2-phenylimidazole and 2-heptadecylimidazole; also suitable are phosphines, metal soaps and acetylacetonates.

Examples of fillers are quartz, bolus alba (china clay), chalk, wollastonite, talc, aluminum oxide trihydrate, and antimony trioxide.

Pigments which can be employed are gas black, phthalocyanine pigments and metal oxides.

In order to improve the resilience of the coating composition, flexibilizers which can be used are butadiene-acrylonitrile rubber and other aliphatic polymers.

Examples of suitable reactive diluents are mono- or polyfunctional alcohols of low molecular mass, which are reacted with epichlorohydrin.

The invention likewise provides for the use of the above-mentioned coating compositions for producing coatings.

The novel coating compositions are preferably used for coating floors, walls, or shaped articles.

The novel coating compositions are likewise suitable for coating steel supports, wood and wood-like materials, cables and pipes.

In the examples below, polyphosphonic/phosphoric esters and the soluble and/or meltable epoxy resins of the first reaction step are prepared, and then flame-retardant coating compositions are prepared and their effectiveness is determined. The insulation capacity of the intumescent paints prepared using these coating compositions was tested in accordance with DIN 4102 Part 2 (1977) in a small-scale test setup according to DIN 4102, Part 8 (1986), while the examination of surface quality was undertaken visually.

The following products were employed in the examples:

®Beckopox EP 140 (Hoechst AG, Frankfurt/Main) This is a low molecular mass condenate of bisphenol A and epichlorohydrin having a density of 1.16 g/ml (at 25° C.), an epoxide equivalent weight of 180–190, an EP value of 0.53–0.55 and a dynamic viscosity of 8000–11,000 mPas (at 25° C.).

®Beckopox EH 625 (Hoechst AG, Frankfurt/Main) This is a solvent-free epoxy resin curing agent based on a modified aliphatic polyamine, having an H equivalent weight of 73 and a dynamic viscosity of 800–1200 mPas (at 25° C.).

®Kronos 2300 (Kronos Titan, Leverkusen) This is a rutile pigment whose surface has been treated with aluminum compounds, having a TiO$_2$ content of $\geq$94%, a density of 4.1 g/cm$^3$ and an oil number of 15–18 g/100 g.

Micro-Talkum 20 M 0 (Bassermann & Co., Mannheim) This is a talc powder with a specific weight of 2.78 g/cm$^3$, a specific surface area of 7 m$^2$/g and a bulk weight of 310 g/l.

Examples 1 to 5 relate to the preparation of the polyphosphonic/phosphoric esters, Examples 6 to 11 to the preparation of soluble and/or meltable epoxy resins, Examples 13 to 20 (Example 12 is a comparison example from the prior art) to the preparation of the novel coatings.

EXAMPLE 1

400 g (3.224 mol) of dimethyl methanephosphonate are charged under an N$_2$ atmosphere to a 2 liter 5-neck flask fitted with thermometer, reflux condenser, powder funnel, stirrer and gas inlet pipe (N$_2$). Over the course of 30 minutes, 376.82 g (1.327 mol) of P$_4$O$_{10}$ are added via the powder funnel, with stirring and cooling, at a rate such that the reaction temperature does not exceed 60° C. After the end of the addition, the mixture is reacted at 70° C. for 5 h more. This gives 776.8 g of a polymethanephosphonic/phosphoric acid methyl ester having a mean chain length of 15, a mean molecular weight of 1365.49 and a phosphorus content of 34.0% by weight.

EXAMPLE 2

The procedure of Example 1 is repeated but reacting 440 g (2.648 mol) of diethyl ethanephosphonate with 322.15 g (1.135 mol) of P$_4$O$_{10}$.

This gives 762.15 g of a polyethanephosphonic/phosphoric acid ethyl ester having a mean chain length of 19, a mean molecular weight of 2014.75 and a phosphorus content of 29.2% by weight.

EXAMPLE 3

The procedure of Example 1 is repeated but reacting 500 g (2.191 mol) of diethyl benzylphosphonate with 272.07 g (0.958 mol) of P$_4$O$_{10}$.

This gives 772.07 g of a polybenzylphosphonic/phosphoric acid ethyl ester having a mean chain length of 22, a mean molecular weight of 2819.41 and a phosphorus content of 24.2% by weight.

EXAMPLE 4

The procedure of Example 1 is repeated but reacting 510 g (2.105 mol) of diethyl o-methylbenzylphosphonate with 251.62 g (0.886 mol) of P$_4$O$_{10}$.

This gives 761.62 g of a poly-o-methylbenzylphosphonic/phosphoric acid ethyl ester having a mean chain length of 17, a mean molecular weight of 2291.28 and a phosphorus content of 23.0% by weight.

EXAMPLE 5

The procedure of Example 1 is repeated but reacting 530 g (2.118 mol) of dimethyl 1-naphthylmethanephosphonate with 244.25 g (0.860 mol) of P$_4$O$_{10}$.

This gives 774.25 g of a poly-1-naphthylmethanephosphonic/phosphoric acid methyl ester having a mean chain length of 14, a mean molecular weight of 1949.65 and a phosphorus content of 22.2% by weight.

EXAMPLE 6

130 g of ®Beckopox EP 140 are charged to a 500 ml five-neck flask with stirrer, thermometer, reflux condenser, dropping funnel and gas inlet pipe (N₂). At 40° C., 16 g of polyphosphonic/phosphoric ester according to Example 1 are added dropwise over the course of 30 minutes. The reaction mixture is subsequently stirred at 100° C. for 4 h more. This gives a colorless and transparent epoxy resin which is flowable at elevated temperature and has an epoxide value of 3.8 mol/kg and a phosphorus content of 3.7% by weight.

EXAMPLE 7

120 g of ®Beckopox EP 140 and 50 ml of methyl ethyl ketone are charged to a 500 ml five-neck flask with stirrer, thermometer, reflux condenser, dropping funnel and gas inlet pipe (N₂). 26 g of polyphosphonic/polyphosphoric ester according to Example 2 in 30 ml of methyl ethyl ketone are added dropwise over the course of 30 minutes. The reaction temperature rises to 50° C. The mixture is stirred for 2 h more. This gives a 69% strength solution of the phosphorus-modified epoxy resin with an epoxide value of 2.0 mol/kg. The phosphorus content of the solvent-free resin is 5.2% by weight.

EXAMPLE 8

The procedure of Example 7 is repeated, but the initial charge to the flask comprises 120 g of ®Beckopox EP 140 and 40 ml of methyl ethyl ketone, and 15 g of polyphosphonic/polyphosphoric ester according to Example 2 in 25 ml of methyl ethyl ketone are added dropwise. This gives an approximately 72% strength solution of the phosphorus-modified epoxy resin having an epoxide value of 2.8 mol/kg. The phosphorus content of the solvent-free resin is 3.2% by weight.

EXAMPLE 9

The procedure of Example 7 is repeated, but the initial charge to the flask comprises 120 g of ®Beckopox EP 140 and 30 ml of methyl ethyl ketone, and 20.5 g of polyphosphonic/polyphosphoric ester according to Example 3 in 25 ml of methyl ethyl ketone are added dropwise. This gives an approximately 76% strength solution of the phosphorus-modified epoxy resin having an epoxide value of 2.7 mol/kg. The phosphorus content of the solvent-free resin is 3.5% by weight.

EXAMPLE 10

The procedure of Example 7 is repeated, but the initial charge to the flask comprises 100 g of ®Beckopox EP 140 and 25 ml of methyl ethyl ketone, and 22 g of polyphosphonic/polyphosphoric ester according to Example 4 in 25 ml of methyl ethyl ketone are added dropwise. This gives a 75% strength solution of the phosphorus-modified epoxy resin having an epoxide value of 2.4 mol/kg. The phosphorus content of the solvent-free resin is 4.1% by weight.

EXAMPLE 11

The procedure of Example 7 is repeated, but the initial charge to the flask comprises 100 g of ®Beckopox EP 140 and 25 ml of methyl ethyl ketone, and 24 g of polyphosphonic/polyphosphoric ester according to Example 5 in 25 ml of methyl ethyl ketone are added dropwise. This gives a 75% strength solution of the phosphorus-modified epoxy resin having an epoxide value of 2.4 mol/kg. The phosphorus content of the solvent-free resin is 4.3% by weight.

EXAMPLE 12

179.25 g (71.7% by weight) of ®Beckopox EP 140 and 70.75 g (28.3% by weight) of ®Beckopox EH 625 were introduced in succession into a stirred vessel and were thoroughly mixed. The resulting coating composition was applied with a roller to one side of a steel panel (St 37) measuring 280×280×6 mm³. The composition cured to completion in one day at 20° C. in air, and its thickness was measured as 1.5 mm.

The coating was clear and its surface was smooth and free of cracks.

Fire testing of the coated panel in accordance with DIN 4102 did not meet the requirements of fire resistance class F 30. During this test, the coating showed no intumescence.

EXAMPLE 13

The procedure of Example 12 was repeated, but the coating composition was prepared by mixing a solution of 220 g of the phosphorus-modified epoxy resin obtained in Example 6, in 160 ml of methyl ethyl ketone, with 61.0 g of ®Beckopox EH 625. After drying for two days at 20° C., the coat thickness was measured as 1.7 mm.

The coating was clear and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

EXAMPLE 14

The coating composition prepared was the same as that in Example 13, but it was applied to the metal panel in a quantity such that, after complete curing, the coat thickness was measured as 2.6 mm.

The coating was clear and the surface of the metal panel to which this coating composition was applied was smooth and free of cracks. Fire testing of the coated panel in accordance with DIN 4102 gave the fire resistance class F 60. In the course of this test, the coating was notable for very good intumescence.

EXAMPLE 15

The coating composition prepared was the same as that in Example 13, but it was applied to the metal panel in a quantity such that, after complete curing, the coat thickness was measured as 7 mm.

The coating was clear and the surface of the metal panel to which this coating composition was applied was smooth and free of cracks. Fire testing of the coated panel in accordance with DIN 4102 gave the fire resistance class F 60. In the course of this test, the coating was notable for very good intumescence.

EXAMPLE 16

The procedure of Example 12 was repeated, but the coating composition was prepared by mixing 230 g of an epoxy resin solution obtained in Example 7 with 33.6 g of ®Beckopox EH 625. After drying for two days at 20° C., the coat thickness was measured as 1.7 mm.

The coating was clear and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

EXAMPLE 17

The procedure of Example 12 was repeated, but the coating composition was prepared by mixing 210 g of an epoxy resin solution obtained in Example 8 with 42.9 g of ®Beckopox EH 625. After drying for two days at 20° C., the coat thickness was measured as 1.6 mm.

The coating was clear and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

EXAMPLE 18

The procedure of Example 12 was repeated, but the coating composition was prepared by mixing 210 g of an epoxy resin solution obtained in Example 9 with 41.4 g of ®Beckopox EH 625. After drying for two days at 20° C., the coat thickness was measured as 1.7 mm.

The coating was clear and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

EXAMPLE 19

The procedure of Example 12 was repeated, but the coating composition was prepared by mixing 220 g of an epoxy resin solution obtained in Example 10 with 38.5 g of ®Beckopox EH 625, 40 g of Kronos 2300 and 110 g of Micro-Talkum 20 M 0. After drying for two days at 20° C., the coat thickness was measured as 1.9 mm.

The coating was an opaque white and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

EXAMPLE 20

The procedure of Example 12 was repeated, but the coating composition was prepared by mixing 220 g of an epoxy resin solution obtained in Example 11 with 38.5 g of ®Beckopox EH 625 and 45 g of Kronos 2300. After drying for two days at 20° C., the coat thickness was measured as 1.7 mm.

The coating was an opaque white and the surface of the metal panel to which this coating composition was applied was smooth and free of cracks. Fire testing of the coated panel in accordance with DIN 4102 gave at least the fire resistance class F 30. In the course of this test, the coating was notable for very good intumescence.

We claim:

1. An expandable, halogen-free, flame-retardant coating composition comprising a curing agent, which composition comprises a soluble, storage stable reaction product of reactants consisting of from 75 to 95 parts by weight of epoxy resin and from 5 to 25 parts by weight of polyphosphoric/polyphosphonic ester, and wherein the overall weight ratio of epoxy resin and polyphosphoric/polyphosphonic ester to curing agent is (1.1 to 10) to 1 and wherein the curing agent is selected from an aliphatic, cycloaliphatic, aromatic heterocyclic amine, polyamidoamines, polyphenols, phenol-aldehyde resins, polycarboxylic acids or their anhydrides, cyanoguanidines, boron trifluorides, or mixtures thereof.

2. An expandable, halogen-free, flame-retardant coating composition as claimed in claim 1, which comprises up to 65 parts by weight of further ingredients and filler.

3. An expandable, halogen-free, flame-retardant coating composition as claimed in claim 1, which comprises from 0.05 to 10% by weight of phosphorus.

4. An expandable, halogen-free, flame-retardant coating composition as claimed in claim 1, which comprises from 2 to 7% by weight of phosphorus.

5. A process for preparing expandable, halogen-free, flame-retardant coating compositions comprising epoxy resins and polyphosphoric/polyphosphonic esters and a curing agent, which comprises reacting, in a first reaction step, reactants consisting of an epoxy resin and a polyphosphoric/polyphosphonic ester to produce a soluble, storage stable reaction product and then, in a second reaction step, converting the reaction product into the coating composition with a curing agent.

6. The process as claimed in claim 5, wherein the first reaction step is carried out in a solvent.

7. The process as claimed in claim 6, wherein the solvent is selected from halogenated hydrocarbons or aliphatic, cycloaliphatic or aromatic hydrocarbons, or mixtures thereof.

8. The process as claimed in claim 6, wherein the solvent is selected from N-methylpyrrolidone, dimethylformamide, tetrahydrofuran, dioxane, dialkyl ethers, glycol ethers, ketones, esters, or mixtures thereof.

9. The process as claimed in claim 6, wherein the reaction in the first reaction step is carried out at temperatures of from −10° to +200° C.

10. The process as claimed in claim 6, wherein the reaction in the first reaction step is carried out at temperatures from 20° to 100° C.

11. The process as claimed in claim 6, wherein the reaction in the first reaction step is carried out at temperatures from 50° to 80° C.

12. The process as claimed in claim 6, wherein the reaction in the second reaction step is carried out at temperatures from 0° to 200° C.

13. The process as claimed in claim 12, wherein the reaction is carried out at temperatures from 30° to 150° C.

14. The process as claimed in claim 12, wherein the reaction is carried out at temperatures from 70° to 120° C.

* * * * *